United States Patent [19]

Wood

[11] Patent Number: 4,575,239

[45] Date of Patent: Mar. 11, 1986

[54] APPARATUS FOR DETECTING DEFECTS IN CAPSULE SHELLS

[75] Inventor: Thomas G. Wood, East Brunswick, N.J.

[73] Assignee: E. R. Squibb & Sons, Inc., Princeton, N.J.

[21] Appl. No.: 412,330

[22] Filed: Aug. 27, 1982

[51] Int. Cl.⁴ .............................................. G01N 21/90
[52] U.S. Cl. ..................................... 356/240; 356/244
[58] Field of Search .............. 356/237, 239, 240, 244, 356/64, 66, 55, 59; 209/588; 362/32

[56] References Cited

U.S. PATENT DOCUMENTS

| | | | |
|---|---|---|---|
| 598,141 | 2/1898 | Ferguson | 356/59 |
| 1,000,644 | 8/1911 | Vanneman | 356/64 |
| 1,236,080 | 8/1917 | Hickman | 356/64 |
| 1,361,040 | 12/1920 | Fox | 356/66 |
| 3,709,598 | 1/1973 | Vandenberg et al. | 356/237 |

Primary Examiner—Vincent P. McGraw
Assistant Examiner—S. A. Turner
Attorney, Agent, or Firm—Lawrence S. Levinson; Burton Rodney

[57] ABSTRACT

Apparatus is provided for use in detecting defects, such as pin holes, cracks and/or uneven gelatin distribution, in capsule shells. The apparatus is comprised of a light box which includes one or a plurality of light bulbs disposed within the box, one or more opaque panels which are disposed in front of each light bulb, and a plurality of openings disposed in the panels, each opening being adapted to receive a capsule body or cap which fits snugly therein and protrudes outwardly away from the light bulbs. Light shining through the capsule shells disposed in the openings indicates defects such as pin holes, cracks and/or uneven distribution of gelatin in the capsules.

8 Claims, 4 Drawing Figures

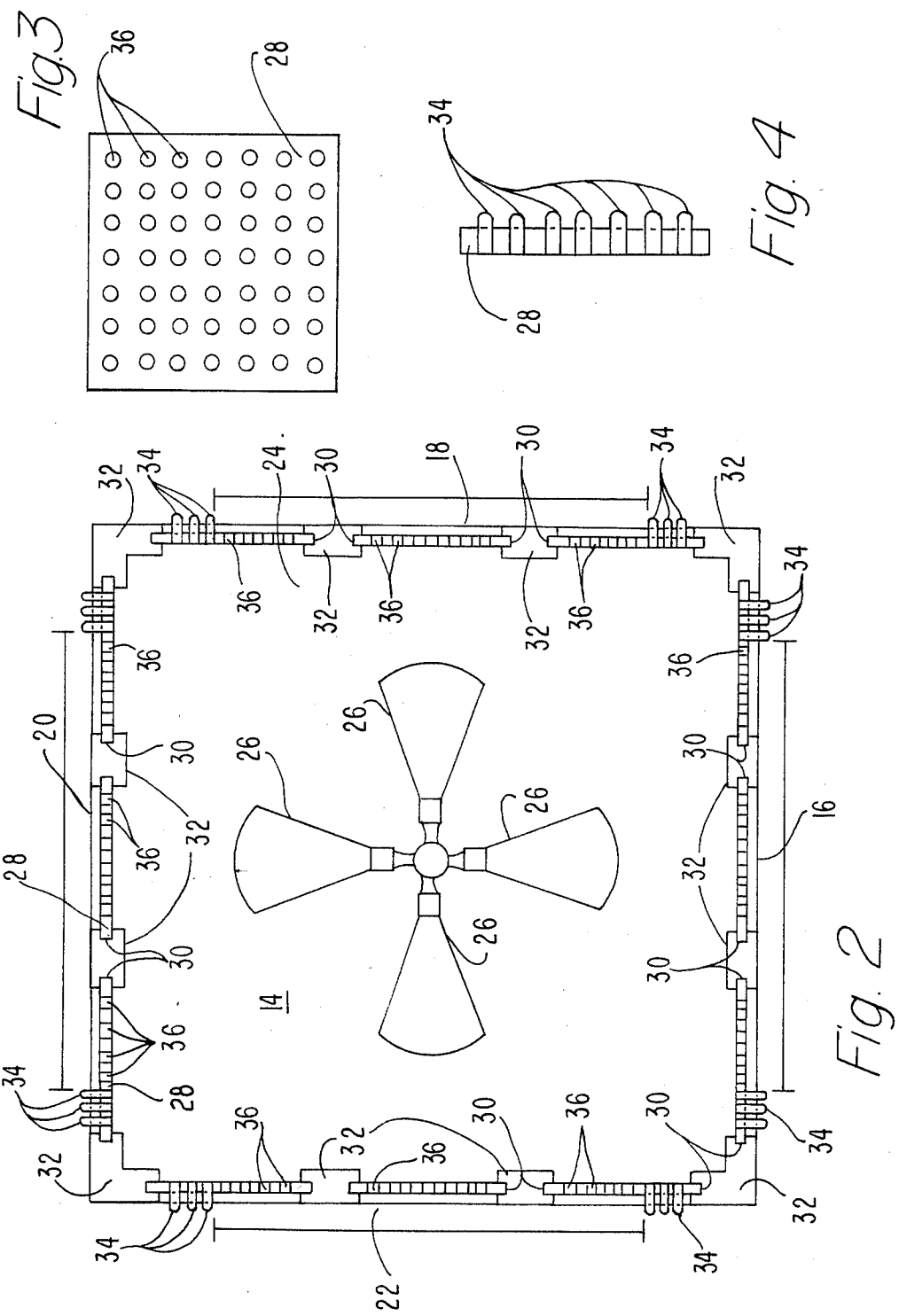

APPARATUS FOR DETECTING DEFECTS IN CAPSULE SHELLS

FIELD OF THE INVENTION

The present invention relates to apparatus for use in detecting defects, such as pin holes, cracks and/or uneven gelatin distribution, in capsule shells.

BACKGROUND OF THE INVENTION

Quality control of capsule bodies and caps is an extremely important matter. Should capsule shells be too brittle they are liable to develop cracks even when subjected to normal wear and tear. The presence of cracks or holes in capsule shells could easily result in leakage and/or spoilage of medication contained in the capsule.

Various quality control tests have been developed by pharmaceutical companies and other manufacturers and vendors of capsule shells for testing for brittleness in empty capsule shells. However, these tests do little for determining if a capsule shell has pin holes or has weakened walls due to uneven gelatin distribution.

REFERENCE TO RELATED PATENT APPLICATIONS

U.S. application Ser. No. 374,567 filed May 3, 1982 discloses apparatus for use in detecting defects in capsule shells which apparatus includes one or more light bulbs disposed within a box, one or more opaque panels which are disposed in front of each light bulb, and a plurality of transparent pegs carried by said panels and protruding outwardly away from the light bulbs, each peg being adapted to carry a capsule body or cap which fits snugly over the peg. Light shining through the capsule shells disposed on the peg indicates defects in the capsules.

Although the above apparatus is an excellent means for detecting defects in capsules, it has been found that where the tip of a capsule to be tested contacts a transparent peg, light passing through the contact point of the peg and capsule may be somewhat distorted making it, at times, difficult to observe all capsule defects.

BRIEF DESCRIPTION OF THE INVENTION

In accordance with the present invention, apparatus is provided for use in detecting defects, such as pin holes, cracks and/or uneven gelatin distribution, in capsule shells comprising, in combination, a box or other enclosed area which includes one or more sides and/or rounded or curved surfaces, and a top and bottom defining an enclosed internal area, one or more light bulbs or other light source (such as, one or more fiber optic elements) disposed and mounted in the internal area, one or more opaque panels comprising one or more sides of the box, the panels being disposed in front of each light source, the panels including a plurality or array of openings each adapted to receive a capsule body or cap which fits into said opening and protrudes outwardly away from the light source.

Light shined through the openings and passed through the capsule shell fitted into openings of said panels is evenly distributed without distortion and nicely shows pin holes, cracks and/or uneven gelatin distribution or other defects in the capsule shells.

BRIEF DESCRIPTION OF THE FIGURES

FIG. 2 is a plan view of the apparatus shown in FIG. 1 wherein the top portion has been removed;

FIG. 3 is a plan view of one of the panels shown in FIG. 1 showing openings into which capsule shells are to be inserted; and FIG. 4 is a side sectional view of one of the panels shown in FIG. 1 including capsule shells fitted into the openings of said panels.

DETAILED DESCRIPTION OF THE INVENTION

Figure 1:
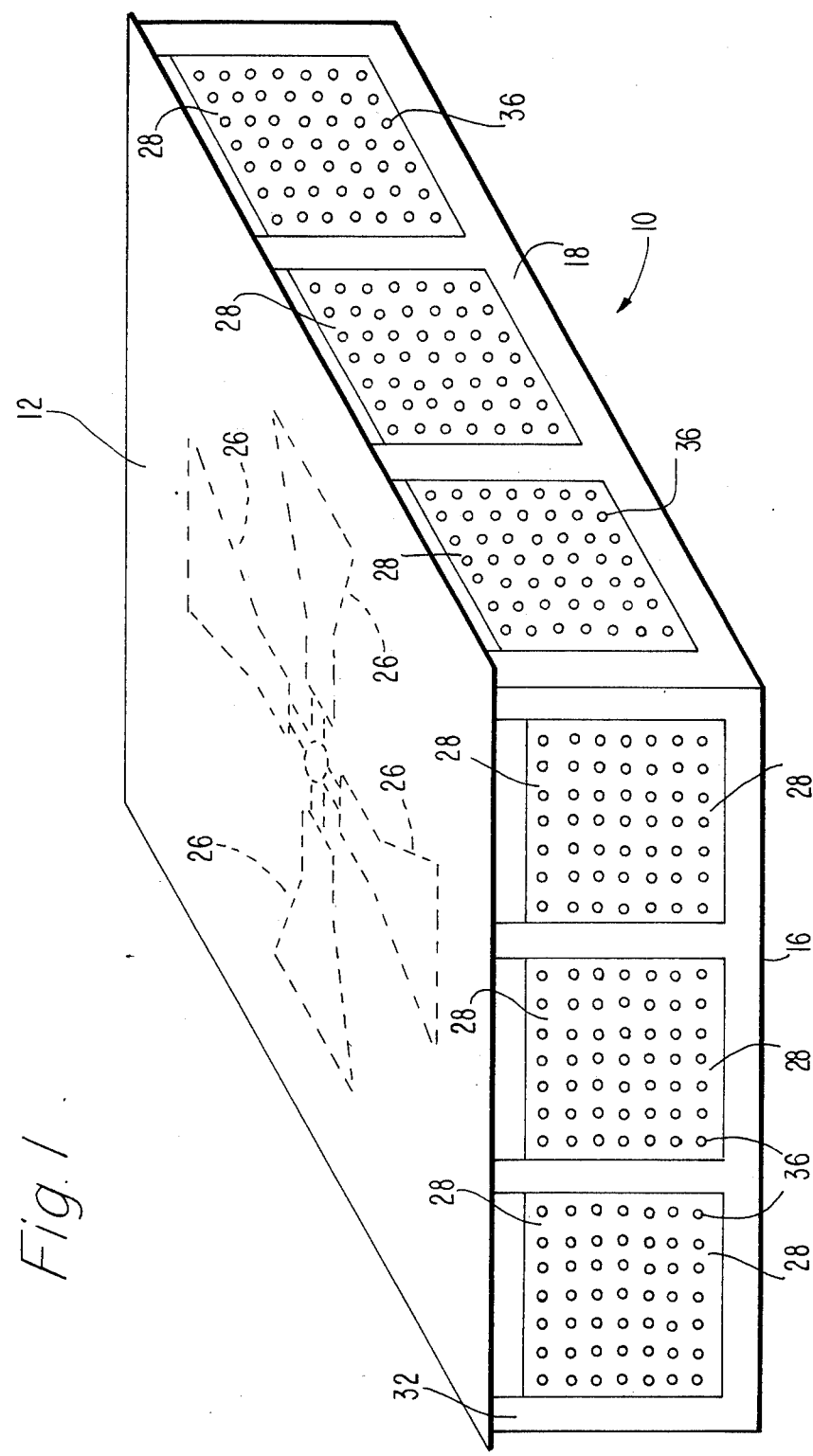
FIG. 1 is a perspective schematic view of an apparatus in accordance with the present invention including top and bottom portions and four sides which include a series of opaque panels having a plurality of openings therein.

Referring now to the accompanying Figures wherein like parts are represented by like numerals in the several views, FIG. 1 illustrates a preferred embodiment of the apparatus of the invention generally indicated by the numeral 10 which is specifically designed for detecting pin holes and uneven gelatin distribution in empty capsules. The apparatus 10, as shown, is formed of a box-like structure which includes top portion 12, bottom portion 14, opaque sides 16, 18, 20 and 22, and internal area 24. Mounted in internal area 24, for example, suspended from the top portion 12 or from a conduit disposed in area 24, are a plurality of spot light bulbs 26 which are positioned so as to face the sides 16, 18, 20 and 22 as shown in FIGS. 1 and 2. The light bulbs are connected to a source of current not shown for sake of drawing clarity.

In the embodiment shown, the sides 16, 18, 20 and 22 are formed of a series of opaque panels 28 which slide into tracks or grooves 30 of panel support members 32 as shown so that the panels are positioned in front of light bulbs 26. Each of the opaque panels 28 includes a plurality of openings 36 best shown in FIG. 3, each opening adapted to receive a capsule shell 34 which protrudes outwardly away from the light sources. The openings 36 are dimensioned so that gelatin capsule bodies or caps 34 fit snugly therein, but so that the capsule shells may be manually rotated in the openings to facilitate detection of defects in the capsule shells as light is passed through the capsule shells. Light emitted from bulbs 26 passes through openings 36 so that if a capsule body or cap 34 positioned in the openings 36 (as shown in FIG. 4) has pin holes and/or uneven gelatin distribution or other defect, light will pass through the capsule body or cap, without any significant distortion, and such defects will be easily observed.

Where the light source employed generates heat, such as light bulbs or spot lights (as opposed to fiber optic elements which emit cool light), it is important that such heat generating light source be disposed at sufficient distance from the capsule shells carried in the openings to avoid melting of the capsule shells. Thus, for example, where the light source is a 150 watt bulb, the openings 36 in panels 28 should be maintained at a distance of at least about 4 to 6 inches from the bulb. It will be appreciated that the distance between the light bulb and the openings will be directly proportional to the wattage of the bulb so that if a 75 watt bulb is employed, the openings may be disposed at least about 2 to 3 inches from the bulb.

A typical apparatus of the invention will have four sides each of which is 2 to 2.5 feet in length and 0.5 to 1.5 feet in height, two to four removable panels for each side, each of the panels being 0.5 to 0.75 feet square and including openings which are spaced 0.75 to 1.25 inches from each other on each panel. However, it will be appreciated that any suitable dimensions will come within the scope of the invention.

In the preferred embodiment shown, the panels 28 are opaque and include a network of openings. The panels, including the openings, may be cast as a single transparent unit and thereafter, the area of the panels surrounding the openings may be spray painted or otherwise made opaque. The panels are easily removable for loading or unloading of capsule shells. However, the panels may also comprise permanent portions of the apparatus. Different panels containing different size openings may also be employed depending on the size of the capsule shells to be tested. In addition, the top portion 12 may also be removable for easy access to the panels 28 and light bulbs 26.

It will be appreciated that the color of the light emitted from the light source should preferably be difficult from the color of the capsule shells to be tested. Thus, different color light bulbs and/or filters may be employed to produce the color light desired.

What is claimed is:

1. A method for detecting defects in capsule bodies and caps, which comprises fashioning an apparatus comprising, in combination, an enclosed area, which is defined by a plurality of external surfaces, and which includes a top portion, a bottom portion and at least three longitudinally disposed sides at least one side of which includes a series of removable vertical panels, each panel of which includes a plurality of openings and is easily removable for loading or unloading of capsule bodies or caps, and a light source which is disposed within the enclosed area, said panels including said openings having solid portions which are opaque, and each of the openings therein being defined by internal walls of said panels dimensioned to snugly carry a capsule body or cap which when seated in said opening will extend horizontally outwardly from said panel but which will snugly fit in said opening and will firmly be held therein so that it will not be easily dislodged, but yet may be manually rotated, positioning capsule bodies, capsule caps or mixtures of separated capsule bodies and caps in said openings, shining light through the openings and said capsule bodies and caps mounted therein and observing if the capsule bodies and caps contain defects.

2. The method as defined in claim 1 wherein said external surfaces include at least three sides each side of which includes a plurality of openings.

3. The method as defined in claim 1 wherein said light source is comprised of a plurality of light bulbs disposed in said enclosed area and positioned to shine light through said openings of said sides.

4. The method as defined in claim 3 wherein said sides comprise a series of panels each panel of which includes a series of bores or openings adapted to receive a capsule body or cap.

5. The method as defined in claim 4 wherein said panels are removable.

6. The method as defined in claim 3 wherein said external surface includes four opaque sides, each side including a series of panels carrying a plurality of openings; and top and bottom portions, and said light source comprises four light bulbs each bulb facing one side.

7. The method as defined in claim 6 wherein each side is comprised of one to four removable opaque panels.

8. The method as defined in claim 1 wherein said sides comprise one or more casted panels including a plurality of openings therein, the area of the panels surrounding said openings being opaque.

* * * * *